United States Patent [19]

Rennecker et al.

[11] Patent Number: 4,554,698
[45] Date of Patent: Nov. 26, 1985

[54] DISPENSING ARRANGEMENT FOR AN UPRIGHT VACUUM CLEANER

[75] Inventors: David B. Rennecker, Canton; Walt S. Taylor, North Canton, both of Ohio

[73] Assignee: The Hoover Company, North Canton, Ohio

[21] Appl. No.: 629,108

[22] Filed: Jul. 9, 1984

[51] Int. Cl.[4] ............................................. A47L 7/04
[52] U.S. Cl. ................................... 15/339; 15/257 B; 55/279; 55/376; 55/473
[58] Field of Search ................. 15/257 B, 339; 55/279, 55/376, 378, 473

[56] References Cited

U.S. PATENT DOCUMENTS

| | | |
|---|---|---|
| 1,614,817 | 1/1927 | Andrew . |
| 1,764,127 | 6/1930 | Stolpe . |
| 1,817,530 | 8/1931 | Spanel . |
| 1,828,584 | 10/1931 | Andersen . |
| 1,863,883 | 6/1932 | Schneider . |
| 1,881,086 | 10/1932 | Marshall . |
| 1,931,165 | 10/1933 | Martinet . |
| 1,970,666 | 8/1934 | Martinet . |
| 1,989,868 | 2/1935 | Kessler . |
| 2,070,643 | 2/1937 | Becker . |
| 2,130,484 | 9/1938 | Cummings . |
| 2,188,428 | 1/1940 | Evans . |
| 2,272,394 | 2/1942 | Armstrong . |
| 2,302,548 | 11/1942 | Heuberger . |
| 2,759,228 | 8/1956 | Gordon . |
| 3,437,424 | 4/1969 | Erbor . |

FOREIGN PATENT DOCUMENTS

| | | |
|---|---|---|
| 2417287 | 1/1961 | France . |
| 342185 | 1/1931 | United Kingdom . |
| 1094832 | 12/1967 | United Kingdom . |

OTHER PUBLICATIONS

Photographs of and advertising brochure for Hoover "Turbopower" Vacuum Cleaner with Scent Dispenser, marketed in Great Britain, Jan. 1983.

Primary Examiner—Chris K. Moore
Attorney, Agent, or Firm—Gerald H. Kreske; A. Burgess Lowe

[57] ABSTRACT

A scent dispensing arrangement is disclosed for use in an upright vacuum cleaner having a flexible air pervious bag extending along a pivoting handle thereof and an air flow generating means which produces an air flow which is exhausted to atmosphere via the bag. A cap member is connected to a top end portion of the flexible bag and interconnected with the pivoting handle for supporting the bag at its uppermost extension along the handle. A scent dispenser is provided which includes a drawer slidably mounted in the cap member for retaining the scented material. The drawer is provided with apertures for providing a path for air flow to atmosphere with sliding movement thereof either opening or closing the path to control dispensing of the scented material.

17 Claims, 6 Drawing Figures

DISPENSING ARRANGEMENT FOR AN UPRIGHT VACUUM CLEANER

BACKGROUND OF THE INVENTION

This invention relates generally to dispensing arrangements and, more particularly, to arrangements for dispensing odorizing or scented materials for use with upright vacuum cleaners.

A vacuum cleaner removes dirt and other foreign particles from a surface being cleaned and deposits them in a dirt collecting bag or other receptacle. However, by the nature of their operation, vacuum cleaners exhaust air which, although filtered, can often contain unpleasant odors which emanate from the particles being picked up. It is well known that such unpleasant odors can be offset or masked by placing or injecting scented material into the air stream of a vacuum cleaner. In canister type vacuum cleaners, there is generally space available within the canister body for mounting of a dispenser. In contrast, an upright vacuum with a relatively compact main body and a handle supported soft air pervious outer bag presents a more difficult dispenser mounting problem.

It is known to mount odorizing dispensers on or in a main body of an upright cleaner with material being dispensed by creating an auxiliary air flow from atmosphere and across the dispensing material. However, such approaches can often be expensive since they often require the cleaners to be specially designed or redesigned to provide for dispenser mounting and the establishment of the necessary air flow channels.

It is also known to provide dispenser arrangements for upright cleaners having impervious bags or casings which surround a dirt collecting filter bag. Dispensers have been attached to an interior wall of such impervious casings so that scented material contained therein is exposed to a portion of the filtered air prior to its being exhausted through an exhaust outlet of the impervious casing. In other known arrangements, all the air from the filter bag is directed through additional filters treated with deodorizing or disinfectant material which are positioned near an exhaust outlet opening of the impervious casing. However, in upright cleaners with soft air pervious outer bags, it is often not desirable to replace soft pervious outer bags with such an impervious casing arrangement because such a change could diminish cleaning performance of the unit due to the accompanying alteration in air flow.

It is also known to dispense odorizing material in an upright cleaner by placement of the material directly in a filter bag thereof or by providing the bag with a side mounted pocket of pervious material into which dispensing material is disposed. Although such arrangements are readily utilized with different types or styles of upright cleaners, they do have certain disadvantages. For example, the rate of dispensing generally cannot be varied to fit particular applications or needs. In addition, termination of dispensing, even for a short duration, requires removal of the dispensing material which is especially difficult if the material has been dropped into the interior of a filter bag.

Thus it would be advantageous to develop a new and improved dispensing arrangement for upright vacuum cleaners having soft air pervious outer bags which can easily be incorporated into existing units without affecting their cleaning performance. It would also be advantageous to develop a dispensing arrangement which could provide selectivity so as to permit the user to control dissemination of odorizing material according to the particular conditions encountered. It would also be highly desirable to provide a dispenser which is readily accessible to the user and one which would permit quick and easy refill and control.

SUMMARY OF THE INVENTION

Accordingly a general object of the present invention is to provide a new and improved dispensing arrangement for use with a vacuum cleaner.

A more specific object of the present invention is to provide a new and improved arrangement for dispensing odorizing material which can be easily and economically incorporated in new or existing upright vacuum cleaners.

Another object of the present invention is to provide a new and improved dispensing arrangement for an upright vacuum cleaner wherein a control is provided to permit a user thereof to quickly and conveniently alter the material dispensing in accordance with conditions encountered.

These and other objects will be readily apparent from the following description taken in connection with the accompanying drawings.

In carrying out the invention in one form thereof, an upright vacuum cleaner is provided with an arrangement for dispensing scented or odorizing material wherein the upright cleaner is provided with a pivoting handle, a flexible bag formed of air pervious material which extends along the handle and an air flow generating means which produces an air flow through the bag. A cap member is provided which is attached to the flexible bag and interconnected with the handle for supporting the bag. The dispenser is located within the cap member and includes an accomodating means for retaining an odorizing material and a means for selectively directing a portion of the air flow through the accommodating means for dispensing the odorizing material contained therewithin.

In one form, the accommodating means comprises a drawer having apertures for providing a path for air flow communication with scented material contained therein. The drawer is slidable within the cap member for either opening or closing the air flow path and thereby controlling the dispensing of scented material.

DESCRIPTION OF THE PREFERRED EMBODIMENT

Figure 1:
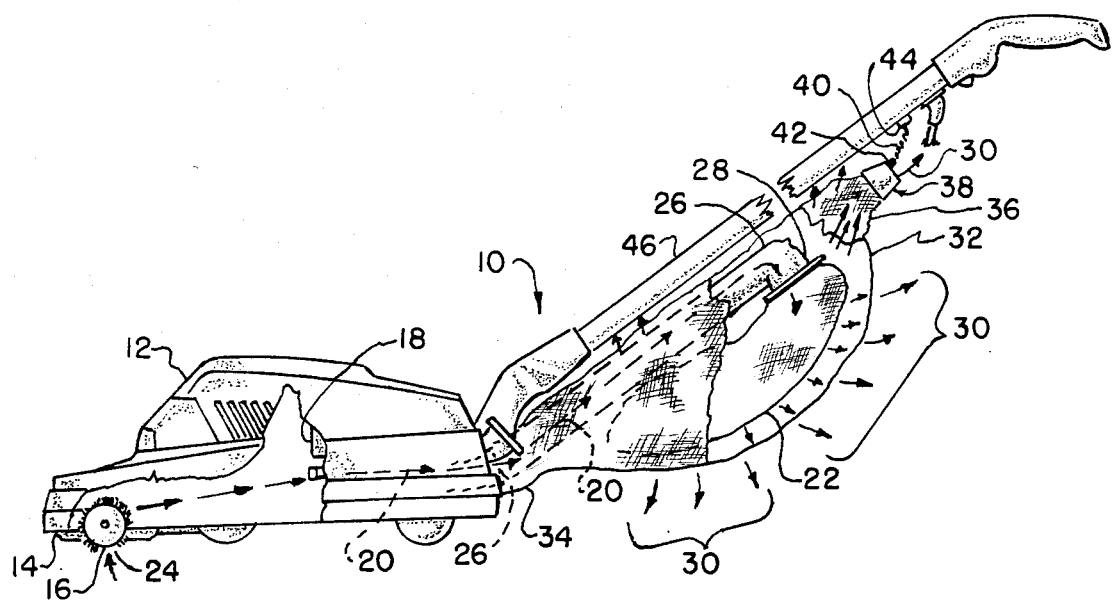
FIG. 1 is a side elevational view, with parts thereof broken away, of an upright vacuum cleaner embodying one form of the invention.

Referring to FIG. 1, there is illustrated an upright vacuum cleaner 10 of one type which embodies features of the present invention in one form. As illustrated, the upright cleaner comprises a conventional main or floor engaging body 12, nozzle 14, rotary agitator 16, and a vacuum generating means or motor-fan unit 18. The motor-fan unit creates a flow of dirt laden air, indicated by arrows 20, through the main body to a dirt collecting filter bag 22. As illustrated, a vacuum pressure is generated at the nozzle to draw the dirt laden air through nozzle opening 24 and then the dirt laden air is pressurized by the motor-fan unit and transmitted from the main body, through an air duct 26 and into the dirt collecting filter bag attached to end portion 28 of the air duct.

The dirt collecting filter bag 22 is formed of air pervious material such as, for example, paper or cloth and functions to filter all the dirt laden air and collect the dirt and dust particles therein. Filtered air, indicated by a plurality of arrows such as, for example, arrows 30, emanates from the filter bag and is exhausted to atmosphere about substantially the entire outer surface or periphery of a flexible outer bag or jacket 32. The outer bag encompasses the inner filter bag and provides support therefor and is formed of air pervious material such as, for example, cloth or a perforated vinyl material. The illustrated outer bag is of a tubular-like construction with its open lower end 34 being clamped about the air duct 26 for support and for providing air flow communication between the main body 12 and the interior of the outer bag. A top or upper end 36 of the outer bag is connected to a bag end or support cap 38 which, in the illustrated arrangement, was formed rigid of a rigid molded acrylonitrile-butadiene styrene (ABS) plastic material although other materials could be utilized. A resilient means, illustrated as spring 40, is connected to eyelet 42 of the bag cap and hook 44 on a pivoting operating handle 46 for support of the outer bag at its uppermost extension alongside the generally vertically extending pivoting handle.

As discussed hereinabove, the filtered air, indicated by arrows 30, is exhausted to atmosphere. Most of this air flows through the outer bag 32 and is exhausted substantially about its entire perimeter; however, as illustrated, a partial amount, or a small portion, of the total can be selectively exhausted to atmosphere via the bag support cap 38 for dispensing a scented or odorizing material as described more fully hereinbelow.

Figure 2:
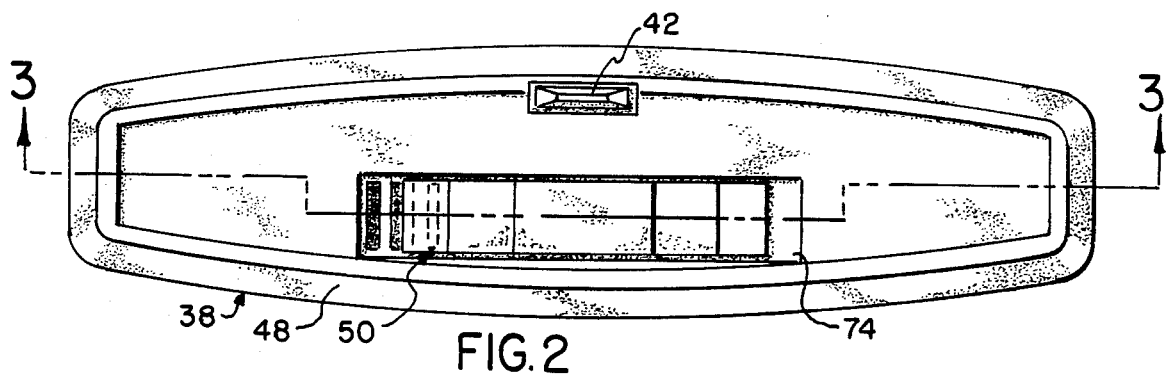
FIG. 2 is a plan view of a bag cap member of FIG. 1 and showing a dispensing arrangement incorporated therein.
Figure 3:
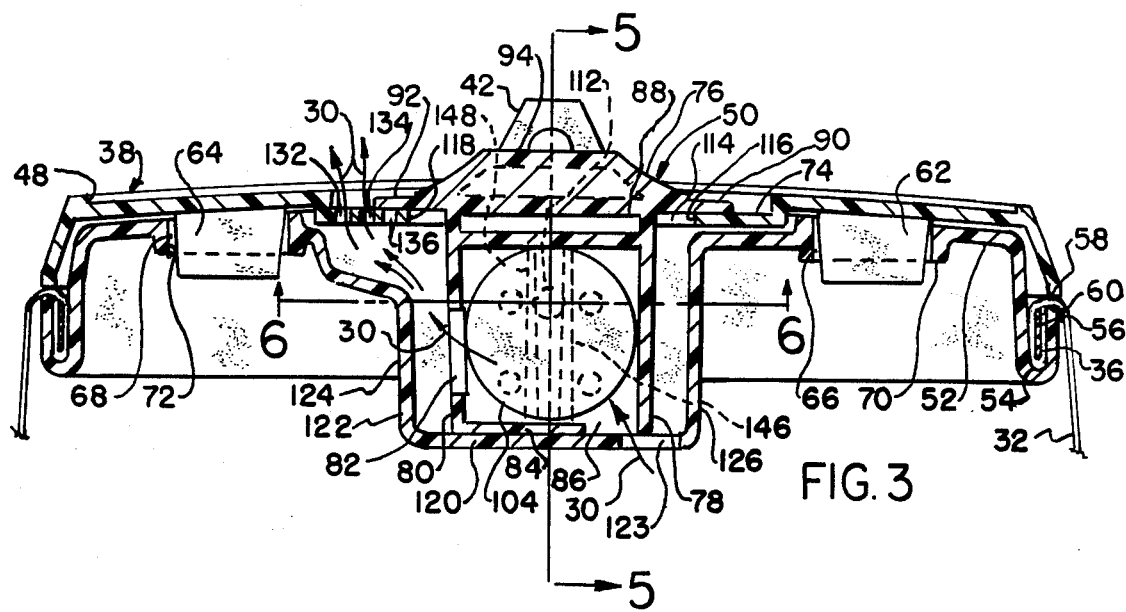
FIG. 3 is a cross sectional view taken along line 3—3 of FIG. 2 and showing details of the dispensing arrangement including control of air flow therethrough.

Referring to FIGS. 2 and 3, the bag cap member 38 includes a top or cover 48 having the hanger or eyelet 42 formed integrally therewith for connection of the spring 40 (FIG. 1). A dispensing arrangement, generally designated by reference numeral 50, is incorporated within the bag cap member. As can be seen in FIG. 3, the cap member also includes a bottom member 52 having a U-shaped channel 54 about its entire outer periphery for receiving the top or upper end 36 of the generally tubular jacket 32. The top end has a plastic retainer strip 56 secured thereto via, for example, heat sealing or sewing with the strip also being received or fitted within the channel. The jacket is clamped or held between edge 58 which extends around the outermost periphery of the cover and edge 60 which extends around the outermost periphery of the bottom member. The clamping or retention of the jacket is accomplished by interlocking the cover and the bottom member in a conventional manner by use of two downwardly extending snap fitting resilient fingers or latches 62 and 64 of the cover although other suitable means such as, for example, bolts or screws could be utilized. The latches extend through respective openings 66 and 68 in the bottom member with each having a not shown projecting offset or tab portion at the ends thereof for engaging respective edge surfaces 70 and 72 which border the respective openings.

Figure 4:
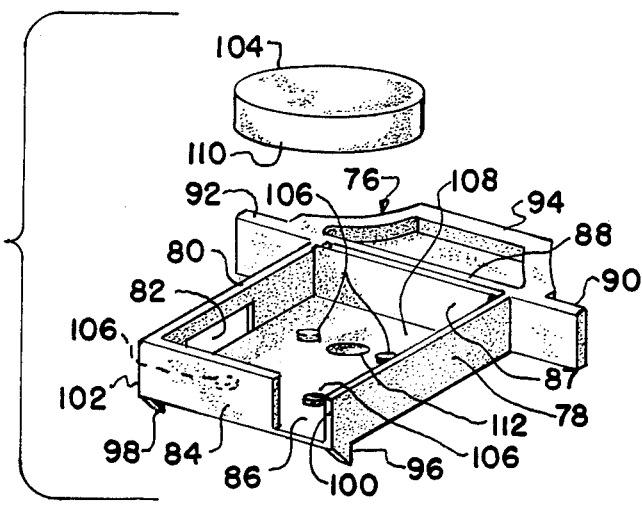
FIG. 4 is a perspective view of a dispensing material accommodating drawer of the dispensing arrangement of FIGS. 2 and 3 and showing a fragrance tablet being positioned therein.

The dispensing arrangement 50 includes a rectangularly shaped recessed portion or guide channel 74 (also see FIG. 2) in the cover 48 for receiving and supporting a scent material accommodated means illustrated as holder or drawer 76. As illustrated in FIG. 4, the drawer includes a side wall 78 and a side wall 80 having an exit aperture 82 therein. The open-top drawer is also provided with a rear wall 84 having an entrance aperture or slot 86 therein, a solid front wall 87 and a front end plate 88 with outer end portions 90 and 92 which extend beyond side walls 78 and 80, respectively. A control handle 94 extends outwardly from the front plate and formed integral therewith to provide means to manipulate or slide the drawer within the guide channel for controlling material dispensing. The drawer further includes two tabs 96 and 98 which extend donwardly at respective rear corners 100 and 102. The tabs provide a means for preventing inadvertent removal of the drawer from the bag cap cover 48 (FIG. 3). A circular tablet or disc 104 of fragrance material to be dispensed is received within the drawer so that it rests upon four spaced-apart posts 106 which extend vertically from the floor or bottom 108 of the drawer. The posts elevate the tablet from the drawer bottom so as to permit air flow about an undersurface 110 of the tablet. Particular fragrance tablets which may be utilized with the dispenser arrangement of the present invention are sold commercially as HOOVER air freshener Part Number 49357-010 or Part Number 57363-003. The tablets are in the form of a cake of fragrance and filler materials. The fragrance material volatizes at low temperature so as to readily mix with the air flowing over the tablet. However, scented materials in other forms could be readily utilized in the dispenser arrangement of the present invention. The bottom of the drawer also includes a dish-shaped area of reduced material thickness forming a detent 112. In a preferred embodiment, the drawer was formed of molded high density polyethylene plastic material although other materials could be utilized.

Figure 5:
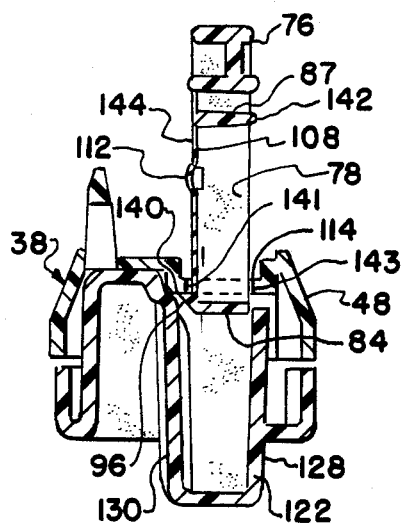
FIG. 5 is a cross sectional view taken along line 5—5 of FIG. 3 with the scent material accommodating drawer being illustrated in a withdrawn or loading position.

Referring again to FIG. 3, the holder or drawer 76 is mounted within the bag cap 38 via insertion through a rectangularly shaped slot 114 in the cover 48 having its lateral extension defined by edges 116 and 118. In the illustrated preferred arrangement, the drawer is supported in the vertical or axial direction by the outer end portions 90 and 92 of the drawer front end plate 88 resting upon the recessed surface or channel portion 74 and the drawer rear wall 84 abutting back wall 120 of a generally rectangularly shaped compartment portion or receptacle 122 in the bottom member 52 of the bag cap; however, successful dispensing arrangements have been fabricated wherein the drawer is supported solely by the rear wall with a slight gap existing between the outer end portions and the recessed surface. Entrance slot 123 in the back wall provides air flow communication with the scent material holder or drawer located within the compartment portion thereby permitting a portion or partial amount of the total air flow to flow toward the scented material 104. The compartment portion also includes a side wall 124, a side wall 126, a top wall 128 (FIG. 5) and a bottom wall 130 (FIG. 5). As illustrated, the receptacle or compartment portion is supported by the bottom member by being formed integrally therewith although they could be formed separately and then attached if desired. Three exhaust slots 132, 134, and 136 are provided in the cover recessed channel portion to permit exhausting to atmosphere of the air flowing from the compartment portion. As can be seen, the drawer width, i.e., the distance between the side walls 78 and 80, is less than the length of the cover slot 114 through which the drawer projects and thus, the drawer is movable relative to the bag cap or slidable in a transverse or lateral direction, i.e., movable to either the right or left as viewed in FIG. 3 between the slot edges 116 and 118. Thus, the sliding drawer having the apertures 82 and 86, the cover recessed portion having the three exhaust slots, and the compartment portion having the rear wall entrance slot 123 cooperate to provide an adjustable air flow control means or a means of selectively directing a portion of the air flow through the drawer to atmosphere for dispensing the fragrance material of the tablet.

In FIG. 3, the drawer 76 is illustrated in a mid or normal dispensing position within the compartment portion 122. In this position, part of the drawer entrance aperture 86 is in partial air communication with the back wall entrance slot 123 thereby providing a path for filtered air, indicated by the arrows 30, to flow into the drawer and about the dispensing tablet 104 for imparting a scent thereto. As indicated by the arrows, the air exits the drawer via the side wall exit aperture 82 and flows to atmosphere via the cover exhaust slots 132 and 134. For full dispensing, the drawer is slid transversely or laterally to the right as viewed in FIG. 3 via its control handle 94 so as to have the drawer rear wall entrance aperture in air full communication with the back wall entrance slot. Such sliding of the drawer also causes the outer end portion 92 to move away from the exhaust slot 136. Thus, a greater amount of air flows through the drawer and is exhausted through all three cover exhaust slots to atmosphere thereby dispensing more material. Dispensing of fragrance material is terminated or inhibited by sliding the drawer to the left, as viewed in FIG. 3, via the control handle 94 so that the path for air flow through the drawer is blocked with the drawer entrance aperture being moved out of communication with compartment rear wall entrance slot; the drawer side wall exit aperture is blocked by the side wall 124 of the compartment portion; and all three of the cover exhaust slots are blocked by the outer end portion 92 of the drawer front plate 88.

In FIG. 5, the drawer 76 has been slidably moved outwardly relative to the bag cap member 38 to its withdrawn or vertical uppermost position whereby a dispensing material tablet 104 (FIG. 4) can be loaded or placed therein. The tabs 96 and 98 (see FIG. 4) engage bottom surface 140 of the cover 48 to prevent inavertent complete removal. If desired, the drawer can be completely removed from the bag cap member by tilting or pivoting the drawer relative to the cover, i.e., tilting the drawer to the left as viewed in the illustration, so as to cause the tabs to disengage the cover bottom surface. The drawer is then pulled outwardly to separate it from the cover. For insertion, the above discussed procedure of removal is reversed. That is, the drawer is tilted or angularly oriented relative to the bag cap member and then inserted through the cover slot 114 with the tabs being moved beyond slot edge 141. The drawer is then pivoted to the generally vertical position as shown in the illustration, whereby it can be slidably moved into the compartment portion 122. To assure retention of the drawer once fully inserted, the drawer front wall 87 is formed slightly higher than the rear wall 84 and side walls 78 and 80 (FIG. 4), and the plastic drawer is formed with sufficient resiliency so that top end 142 of the front wall deflects to move past slot edge 143 and engages the cover bottom surface therebeyond for a snap fit of the drawer. This snap fit prevents the drawer from falling out during vacuum cleaner operation, but a slight outward pull on the drawer releases the snap fit connection and allows the drawer to be easily slid outwardly for loading or removing a dispensing tablet. As can be seen in the illustration, the drawer is provided with the detent 112 extending from rear surface 144 of the drawer bottom 108.

Figure 6:
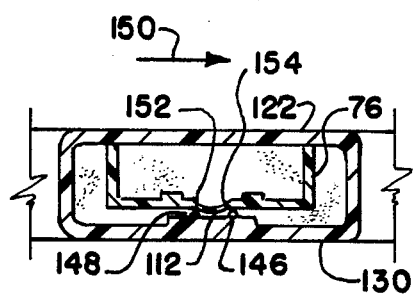
FIG. 6 is a cross sectional view taken along line 6—6 of FIG. 3 and showing details of a detent arrangement for maintaining a selected material dispensing control position.

As illustrated in FIG. 6, the drawer detent 112 cooperates with ribs 146 and 148 (detent and ribs are also shown dotted in FIG. 3) which extend parallel to each other and vertically along the bottom wall 130 of the compartment portion 122. The detent and ribs provide a means of maintaining the drawer 76 in any one of three discrete selected transverse or lateral positions so as to maintain a selected dispensing rate. In FIG. 6, the detent is positioned between the two ribs and engaged thereby so as to maintain the drawer in a mid position within the compartment portion which is a normal dispensing position with air flow therethrough being as previously described in connection with FIG. 3. A high dispensing rate is selected by sliding of the drawer transversely in a direction indicated by arrow 150. The detent has sufficient resiliency to deflect upwardly during the transverse or lateral drawer movement so as to permit it to ride over the rib 146. Thus, with the drawer in a high air flow or high dispensing positon, the rib 146 engages side 152 of the detent for maintaining the drawer in the selected high dispensing position. For termination of dispensing from the normal position illustrated in FIG. 6 the drawer is moved in a transverse direction opposite to the direction indicated by arrow 150 so that the detent is deflected inwardly to ride or move over the rib 148. After movement over the rib, the resilient detent restores itself to its original configuration and the drawer is maintained in the selected off dispensing position by the rib 148 engaging side 154 of the detent. The detent in the illustrated embodiment was established by providing an integral dish-shaped deformation of reduced thickness in the bottom of the drawer which was fabricated of plastic material. However, other suitable detent arrangements or configurations could be provided.

While there has been shown and described herein a preferred embodiment of the present invention, it should be apparent to persons skilled in the art that numerous modifications may be made therein without departing from the true spirit and scope of the invention. Accordingly, it is intended by the appended claim to cover all modifications which come within the spirit and scope of this invention.

We claim:

1. An upright vacuum cleaner comprising:
   a pivoting handle;

a flexible bag formed of air pervious material and extending along said pivoting haandle;

air flow generating means for producing an air flow through said flexible bag;

a cap member attached to said flexible bag and interconnected with said pivoting handle for supporting said flexible bag; and a dispenser located in said cap member including accommodating means for retaining an odorizing material and means for selectively directing a portion of the air flow through said accommodating means for dispensing an odorizing material being retained thereby.

2. The upright vacuum cleaner of claim 1 wherein said cap member includes a compartment portion having said accommodating means received therewithin and wherein said accommodating means and said cap member are movable relative to each other for permitting placement of an odorizing material in said accommodating means.

3. The upright vacuum cleaner of claim 2 further including means for preventing inadvertent removal of said accommodating means from said cap member.

4. The upright vacuum cleaner of claim 1 wherein said accommodating means is provided with apertures which provide a path for air flow therethrough and wherein said means for selectively directing a portion of the air flow either permits air flow through the apertures for dispensing odorizing material or blocks the air flow path through said accommodating means for inhibiting dispensing of odorizing material.

5. The upright vacuum cleaner of claim 1 wherein said accommodating means is movable relative to said cap member for controlling air flow communication with dispensing material being retained thereby.

6. The upright vacuum cleaner of claim 5 and further including means of maintaining said accommodating means in discrete selected positions within the cap member.

7. An upright vacuum cleaner comprising:
a pivoting handle;
a flexible bag formed of pervious material, extending along said pivoting handle and including a top end portion;
air flow generating means for producing an air flow through said flexible bag for exhaust to atmosphere;
a bag support member connected to the top end portion of said flexible bag and interconnected with said pivoting handle for supporting said flexible bag at its uppermost extension along said pivoting handle;
a dispenser mounted in said bag support member including accommodating means for retaining a material to be dispensed and control means for selectively permitting a portion of the air flow to exhaust to atmosphere via said accommodating means for dispensing material retained thereby.

8. The upright vacuum cleaner of claim 7 wherein said control means is adjustable for controlling air flow through said accommodating means thereby controlling the rate at which material is dispensed.

9. The upright vacuum cleaner of claim 7 including means of maintaining said control means in a selected position.

10. An upright vacuum cleaner comprising:
a pivoting handle;
a flexible air pervious bag extending along said pivoting handle and including a top end portion;
air flow generating means for producing an air flow through said flexible bag for exhaust to atmosphere;
a bag cap member connected to the top end portion of said flexible air pervious bag and interconnected with said pivoting handle for supporting said flexible air pervious bag at its uppermost extension along said pivoting handle;
a holder slidably mounted in said bag cap member for retaining a scented material and for selectively directing a portion of the air flow to atmosphere via said holder for dispensing scented material being retained thereby.

11. The upright vacuum cleaner of claim 10 wherein said holder includes apertures which provide a path for air flow therethrough to atmosphere and wherein sliding movement of said holder either opens or closes the path therethrough to atmosphere.

12. The upright vacuum cleaner of claim 10 wherein said holder comprises a drawer which is slidable outwardly from said cap member so as to permit loading of a scented material therein for dispensing.

13. An upright vacuum cleaner comprising:
a main body including a nozzle for engaging a surface to be cleaned;
a handle pivotally connected to said main body;
an air pervious flexible bag having a top end and an open lower end for permitting air communication between its interior and said cleaner main body;
air flow generating means for producing an air flow from the nozzle, through said main body into said flexible air pervious bag and through said flexible air pervious bag for exhausting to atmosphere about substantially the entire outer surface of the bag;
a rigid bag cap member connected to the top end of said flexible air pervious bag and interconnected with said pivoting handle for supporting the top end of said flexible air pervious bag; and
a receptacle supported by said rigid bag cap member for receiving a scented material, said receptacle providing for air flow therethrough whereby a portion of the total air flow passes to atmosphere via said receptacle for imparting a scent to the exhaust air.

14. The upright vacuum cleaner of claim 13 further including control means for selectively controlling air flow through said receptacle.

15. The upright vacuum cleaner of claim 13 further including a holder mounted within said receptacle for supporting scented material.

16. The upright vacuum cleaner of claim 15 wherein said holder is removable from said receptacle so as to permit loading of scented material into said holder.

17. The upright vacuum cleaner of claim 15 wherein said holder is slidable within said receptacle for controlling air flow communication with scented material being retained thereby.

* * * * *